United States Patent [19]

Langer et al.

[11] Patent Number: 4,475,551

[45] Date of Patent: Oct. 9, 1984

[54] ARRHYTHMIA DETECTION AND DEFIBRILLATION SYSTEM AND METHOD

[75] Inventors: Alois A. Langer, Pittsburgh; Marlin S. Heilman, Gibsonia, both of Pa.

[73] Assignee: Mieczyslaw Mirowski, Owings Mills, Md.

[21] Appl. No.: 414,353

[22] Filed: Sep. 2, 1982

Related U.S. Application Data

[63] Continuation of Ser. No. 175,670, Aug. 5, 1980, abandoned.

[51] Int. Cl.³ ............................................. A61N 1/36
[52] U.S. Cl. ................................ 128/419 D; 128/705
[58] Field of Search ..................................... 126/419 D

[56] References Cited

U.S. PATENT DOCUMENTS 3,614,955 10/1971 Mirowski et al. .............. 128/419 D
4,202,340 5/1980 Langer et al. .................. 128/419 D

OTHER PUBLICATIONS

Stratbucker et al., "Rocky Mountain Engineering Society", 1965, pp. 57-61.

*Primary Examiner*—William E. Kamm
*Attorney, Agent, or Firm*—Fleit, Jacobson, Cohn & Price

[57] ABSTRACT

The invention relates to an arrhythmia detection system and method for defibrillating the heart of a patient experiencing abnormal cardiac rhythm, wherein the abnormal cardiac rhythm (comprising one of fibrillation, high rate tachycardia, and low rate tachycardia) is first detected, the heart rate is sensed so as to distinguish between fibrillation and high rate tachycardia, on the one hand, and low rate tachycardia, on the other hand, and automatic defibrillation of the heart of the patient is implemented when one of fibrillation and high rate tachycardia is determined. In one embodiment, base and apical electrodes are connected to a probability density function (PDF) circuit and a rate circuit. When both abnormal cardiac rhythm and excessively high heart rate are detected, defibrillation of the heart of the patient is implemented. In a second embodiment, a sensing button is also connected to the heart, and a switch is interposed between the electrodes and sensing button, on the one hand, and the interface, on the other hand. During monitoring of cardiac rhythm by the PDF circuit, the switch automatically connects the electrodes to the PDF circuit, while, during sensing of the heart rate, the switch connects the sensing button to the heart rate circuit. Upon detection of the need for defibrillation, the switch automatically connects the defibrillation pulse generator to the electrodes. Further features include a timed reset capability.

37 Claims, 7 Drawing Figures

ARRHYTHMIA DETECTION AND DEFIBRILLATION SYSTEM AND METHOD

The present application is a continuation of prior U.S. patent application Ser. No. 175,670, filed Aug. 5, 1980, now abandoned.

BACKGROUND OF THE INVENTION

1. Field of the Invention

The present invention relates to an arrhythmia detection system and method, and more particularly to an improved system and method for defibrillating the heart of a patient when the patient experiences life-threatening fibrillation.

2. Description of the Prior Art

In recent years, substantial progress has been made in the development of defibrillation techniques for providing an effective medical response to various heart disorders or arrhythmias particularly ventricular fibrillation which is characterized by an irregular ECG waveform. Earlier efforts resulted in the development of an electronic standby defibrillator which, in response to detection of abnormal cardiac rhythm, discharged sufficient energy, via electrodes connected to the heart, to depolarize the heart and restore it to normal cardiac rhythm. Examples of such electronic standby defibrillators are disclosed in commonly assigned U.S. Pat. No. 3,614,954 (subsequently, U.S. Pat No. Re. 27,652) and U.S. Pat. No. 3,614,955 (subsequently, U.S. Pat. No. Re. 27,757).

Past efforts in the field have also resulted in the development of implantable electrodes for use in accomplishing ventricular defibrillation (as well as other remedial techniques). In accordance with such techniques, as disclosed (for example) in U.S. Pat. No. 4,030,509 of Heilman et al, an apex electrode is applied to the external intrapericardial or extrapericardial surface of the heart, and acts against a base electrode which can be either similarly conformal or in the form of an intravascular catheter. Such electrode arrangements of the prior art, as disclosed in the aforementioned patent of Heilman et al, can employ independent pacing tips associated with either a base electrode or an apex electrode, or both.

Recent efforts also have resulted in the development of techniques for monitoring heart activity (for the purpose of determining when defibrillation or cardioversion is necessary), which techniques employ a probability density function for determining when ventricular fibrillation is present. Such a technique, employing the probability density function, is disclosed in U.S. Pat. Nos. 4,184,493 and 4,202,340, both of Langer et al.

In accordance with this latter technique of the prior art, when the probability density function is satisfied, fibrillation of the heart is indicated. However, recent experience has shown that, with one or more particular abnormal ECG patterns, the prior art probability density function detector, if not optimally adjusted, can be "triggered" not only by actual ventricular fibrillation, but also by some forms of high rate ventricular tachycardia, and low rate ventricular tachycardia as well, particularly in the presence of ventricular conduction abnormalities. Unlike ventricular fibrillation, such high rate and low rate tachycardias are characterized by regular R-waves occurring at generally stable rates. The possibility of such triggering in the presence of high rate tachycardia is acceptable because high rate tachycardia can be fatal if present at such a rate that sufficient blood pumping no longer is accomplished. However, triggering in the presence of non-life threatening, low rate tachycardia could be considered a problem. Therefore, it has been determined that there is a need for a system and method for distinguishing between ventricular fibrillation and high rate tachycardia, on the one hand, and low rate tachycardia, on the other hand.

It is worth noting that prior art implementation of the probability density function technique was, for a time, limited to "triggering" only in the presence of ventricular fibrillation. This was accomplished by adjusting the decision boundaries of the probability density function detector in a conservative way so as to "trigger" only upon occurrence of life-threatening ventricular fibrillation. However, it was soon realized that there existed situations in which it was desirable to take remedial action upon the detection of high rate tachycardia, as indicated by occurrence of a heart rate above a lower threshold level (for example, above 200 beats per minute). This was initially accomplished merely by adjusting the probability density function criteria so as to be "triggered" at the lower threshold level.

However, it was soon discovered that a problem existed in a detector with relaxed decision criteria, in that extraordinary types of ECG signals were capable of "triggering" the modified probability density function detector, even though neither ventricular fibrillation nor high rate tachycardia was present. Therefore, it has been determined that there is a need for an arrhythmia detection system and method which not only performs a probability density function analysis, but which also includes some technique for distinguishing between fibrillation and high rate tachycardia, on the one hand, and low rate tachycardia, on the other hand. Thus, the inventive system and method herein disclosed amounts to a "backup" technique by means of which high rate tachycardia is treated by issuance of a defibrillating shock to the patient, while low rate tachycardia is not so treated.

SUMMARY OF THE INVENTION

According to the present invention, there is provided an arrhythmia detection system and method, and more particularly an improved system and method for defibrillating a heart which is undergoing abnormal cardiac rhythm, the improved system and method employing a technique for distinguishing between ventricular fibrillation and high rate tachycardia, on the one hand, and low rate tachycardia, on the other hand. More specifically, the system and method of the present invention, besides utilizing the probability density function technique to determine the presence of abnormal cardia rhythm, also employs heart rate sensing for the purpose of distinguishing between ventricular fibrillation and high rate tachycardia, on the one hand, the latter being indicated by a heart rate above a predetermined threshold, and low rate tachycardia, on the other hand, the latter being indicated by a heart rate falling below the predetermined threshold.

The present invention is implemented by a first preferred embodiment of a system, wherein a superior vena cava (or base) electrode and an apical (or patch) electrode are associated with the heart, and are employed, as in conventional in the art, not only to derive an electrocardiograph (ECG) signal, but also to apply a defibrillating shock to the heart. It should be noted that the ECG amplifier in the first embodiment essentially provides the derivative of the heart signal as taught in U.S. Pat. No. 4,184,493. However, in contrast to the prior art, the differentiated ECG signal is, in this first embodiment of the invention, applied to a probability density function circuit, and to a low pass filter and a heart rate circuit, by means of which the probability density function and heart rate, respectively, are obtained. In accordance with this first embodiment, satisfaction of the probability density criteria (that is, determination of whether the time-averaged derivative of the ECG remains off the base line for extended periods of time) while the heart rate is above a predetermined threshold results in actuation of a conventional defibrillating pulse generator to issue a defibrillating shock to the heart. Thus, the defibrillating shock will be issued to the heart only upon the occurrence of fibrillation or high rate tachycardia, as contrasted with non-life threatening low rate tachycardia.

In accordance with a second embodiment of the present invention, a sensing button (preferably, associated with the apical or patch electrode) is connected to the heart for use in deriving the heart rate. Thus, in this embodiment, the base and apical electrodes are utilized initially to derive the ECG signal by means of which the probability density function is examined. If the probability density function indicates abnormal cardiac rhythm, a switching operation takes place, whereby the sensing button is utilized to derive an ECG signal which is further utilized to determine the heart rate. Since a very small area electrode will result in signals in which cardiac depolarizations can still be identified, even during ventricular fibrillation, a conventional R-wave detector can be used so as to provide an R-wave for heart rate sensing. Then, if the heart rate is above the predetermined threshold, a defibrillating shock is issued. Once a shock is issued, a further switching operation is executed so that the base and apical electrodes may be utilized in further examining the probability density function.

In accordance with a further feature of the present invention, this second embodiment is provided with a timed reset capability, whereby, once the probability density function indicates abnormal cardiac rhythm, if a heart rate above the predetermined threshold is not indicated within a predetermined time, a return switch operation is automatically executed so as to permit renewed monitoring of the base and apical electrodes and examination of the resulting ECG signal vis-a-vis the probability density function.

Therefore, it is an object of the present invention to provide an arrhythmia detection system and method, and more particularly an improved system and method for defibrillating a heart experiencing abnormal cardiac rhythm.

It is a further object of the present invention to provide a system and method which is capable of distinguishing between ventricular fibrillation and high rate tachycardia, on the one hand, and low rate tachycardia, on the other hand.

It is a further object of the present invention to provide a system and method which employs a probability density function technique to determine the existence of abnormal cardiac rhythm, and which further employs a heart rate sensing technique for the purpose of distinguishing between ventricular fibrillation and high rate tachycardia, on the one hand, and low rate tachycardia, on the other hand.

It is a further object of the present invention to provide a system and method, wherein base and apical electrodes are employed both for monitoring the ECG signal vis-a-vis the probability density function, and for determining whether or not the heart rate is above or below a predetermined threshold.

It is an additional object of the present invention to provide a system and method which employs base and apical electrodes for monitoring the ECG signal in conjunction with examining the ECG signal vis-a-vis the probability density function, and which employs a sensing button to derive heart rate information for distinguishing between ventricular fibrillation and high rate tachycardia, on the one hand, and low rate tachycardia, on the other hand.

It is an additional object of the present invention to provide a system and method, wherein the probability density function is first examined to determine whether or not abnormal cardiac rhythm exists, and wherein, if such abnormal cardiac rhythm does exist, the heart rate of the patient is then examined to distinguish between ventricular fibrillation and high rate tachycardia, on the one hand, in which case a defibrillation pulse is issued, and low rate tachycardia, on the other hand, in which case a defibrillation pulse is not issued.

It is an additional object of the present invention to provide a system and method with a timed reset capability, wherein, once the probability density function indicates abnormal cardiac rhythm, if a heart rate exceeding a predetermined threshold is not detected within a predetermined amount of time, the system and method return to monitoring of the ECG signal vis-a-vis the probability density function, and no defibrillation pulse is issued.

The above and other objects that will hereinafter appear, and the nature of the invention, will be more clearly understood by reference to the following description, the appended claims, and the accompanying drawings.

DETAILED DESCRIPTION

The arrhythmia detection system and method of the present invention will now be described in more detail with reference to FIG. 1, which is a block diagram of a first embodiment of the system.

Figure 1:
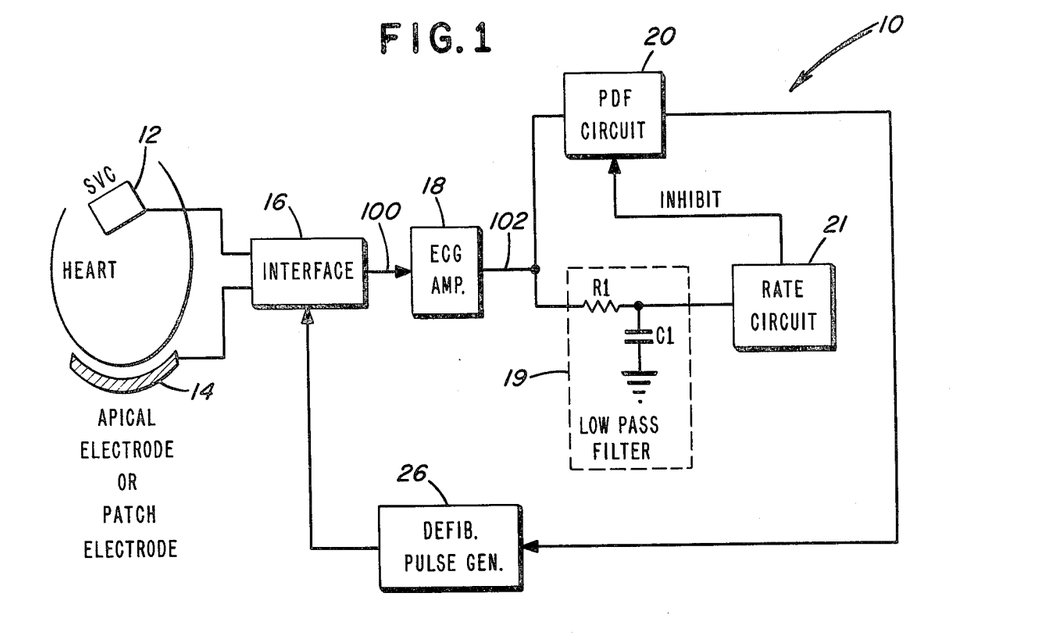
FIG. 1 is a block diagram of a first embodiment of the arrhythmia detection system of the present invention.

Referring to FIG. 1, the system of the present invention (generally indicated by reference numeral 10) is connected to a superior vena cava (or base) electrode 12 and an apical (or patch) electrode 14, the latter being disposed in contact with the heart of the patient as is known in the prior art (see, for example, U.S. Pat. No. 4,030,509 of Heilman et al mentioned above). In the system 10, electrodes 12 and 14 are connected, via an interface 16, to an ECG amplifier 18 which has inherent filtering so as to provide an approximation of the differentiated ECG.

The ECG amplifier 18 is connected both to low pass filter circuit 19 (which itself is connected to heart rate circuit 21) and to probability density function (PDF) circuit 20. Heart rate circuit 21 is connected via its inhibit output line (INHIBIT) to the PDF circuit 20, by means of which the output line heart rate circuit 21 is able to inhibit output from the PDF circuit 20. The output of the PDF circuit 20 is connected to defibrillation pulse generator 26, the latter being connected via the interface 16 to the electrodes 12 and 14.

In operation, electrodes 12 and 14 are employed, via the interface 16 (a conventional interface, or isolation circuit), for two purposes: (1) monitoring of heart activity via ECG amplifier 18, which develops a differentiated ECG signal output provided to PDF circuit 20 and low pass filter 21, respectively; and (2) application of a defibrillating shock from defibrillation pulse generator 26, via the interface 16, to the heart. More specifically, PDF circuit 20 monitors the probability density function of the differentiated ECG output signal of ECG amplifier 18, and, in accordance with conventional techniques (as disclosed, for example, in U.S. Pat. Nos. 4,184,493 and 4,202,340 of Langer et al), determines when abnormal cardiac rhythm of the heart exists. At the same time, the low pass filtered ECG signal, provided as the output of low pass filter 19, is employed by rate circuit 21 to determine when the heart rate exceeds a predetermined threshold, at which time rate circuit 21 removes its inhibiting influence on PDF circuit 20.

Thus, upon determination of abnormal cardiac rhythm by PDF circuit 20, and of a heart rate above the predetermined threshold by rate circuit 22, the PDF circuit 20 is allowed to enable defibrillation pulse generator 26, causing the latter to apply a defibrillating shock, via interface 16, to the heart.

Figure 2:
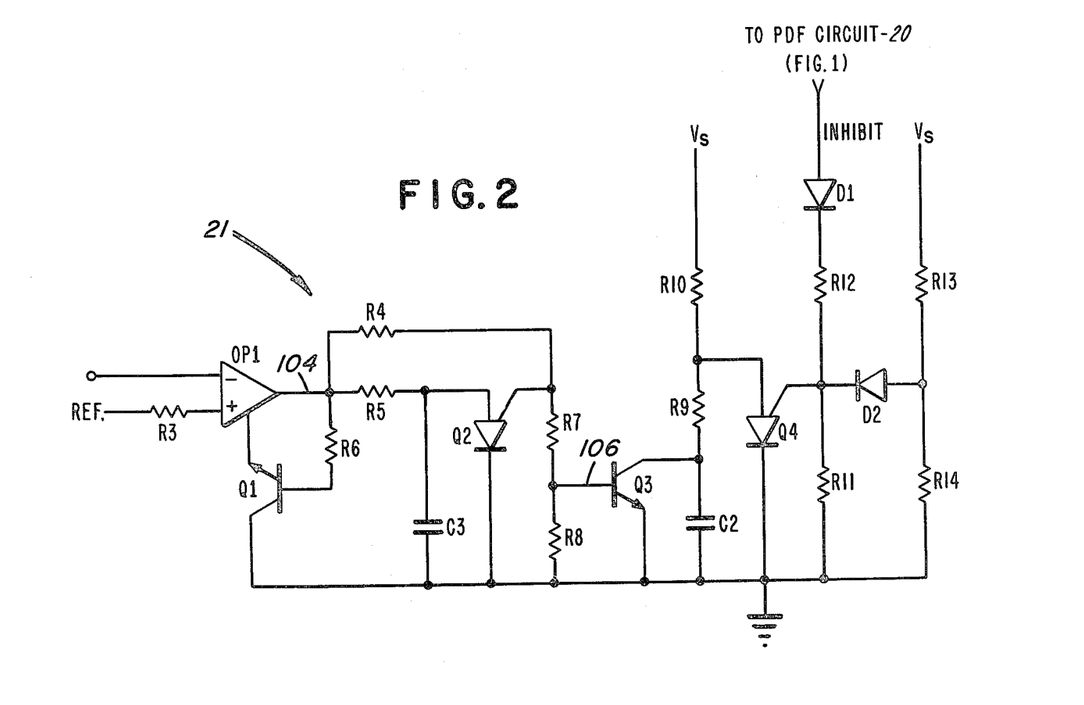
FIG. 2 is a detailed diagram of the heart rate circuit employed for detecting heart rate in the embodiment of FIG. 1.
Figure 3A:
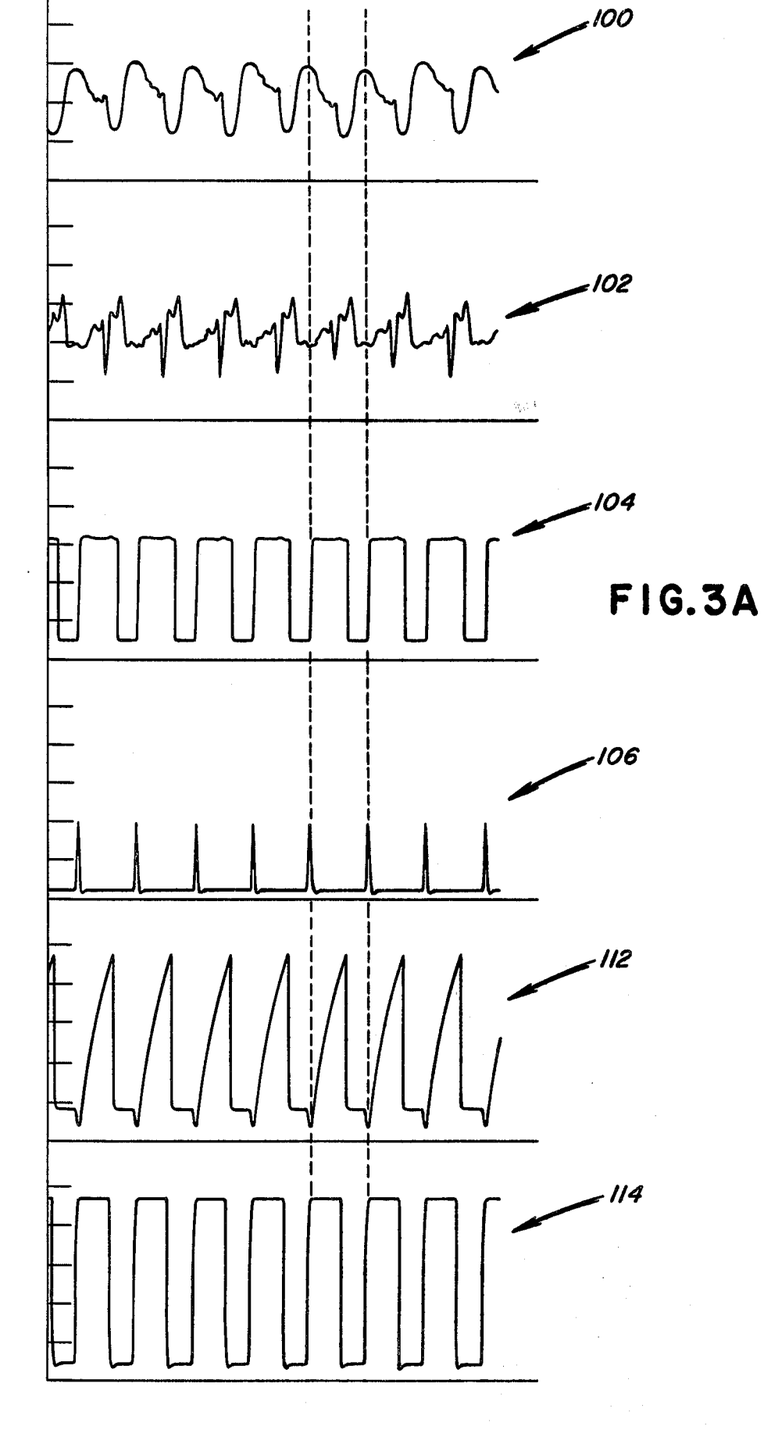
FIG. 3A and 3B are a series of waveform diagrams utilized in describing the operation of the heart rate circuit of FIG. 2.
Figure 3B:
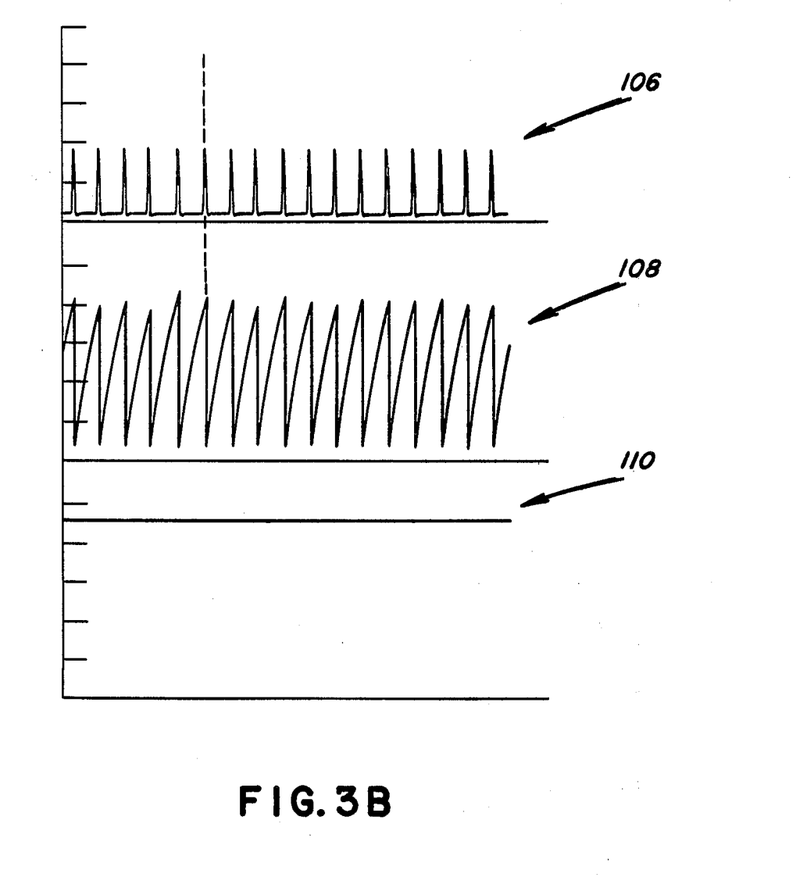

FIG. 2 is a detailed diagram of the heart rate circuit employed for detecting heart rate in the embodiment of FIG. 1, while FIGS. 3A and 3B are a series of waveform diagrams utilized in describing the operation of the heart rate circuit of FIG. 2.

As seen in FIG. 2, the heart rate circuit 21 comprises operational amplifier OP1 (which is used as a comparator), transistors Q1 through Q4, resistors R3 through R14, capacitors C2 and C3, and diodes D1 and D2.

In operation, the heart rate circuit 21 of FIG. 2 functions in the following manner, with reference to the waveforms shown in FIG. 3. As previously mentioned, the input to ECG amplifier 18 (FIG. 1) comprises an undifferentiated ECG signal, as provided by the electrodes 12 and 14. The undifferentiated ECG signal is represented by the waveform 100 of FIG. 3A, and is illustrated as a signal having regular R-waves and a generally stable (or uniform) rate.

As also previously mentioned, the ECG amplifier 18 amplifies and filters (differentiates) the ECG signal, and the amplified and differentiated output of the ECG amplifier 18 is shown as waveform 102 in FIG. 3A. Finally, prior to being provided as an input to the heart rate circuit 21, the amplified and differentiated ECG signal from amplifier 18 is filtered, in a manner to be discussed in more detail below, by low pass filter 19 (made up of resistor R1 and capacitor C1).

Referring to FIG. 2, the amplified, differentiated and filtered ECG signal is provided to the negative input of operational amplifier OP1, the positive input of which receives a reference input REF via resistor R3. Operational amplifier OP1 is used as a comparator, and switches between low and high outputs in accordance with the relationship between the ECG input and the reference REF. More specifically, it should be noted that zero crossings in a derivative waveform (such as the output of amplifier 18 of FIG. 1) correspond to peaks in the original signal (the original ECG signal). Accordingly, low pass filter 19 of FIG. 1 filters the differentiated ECG input provided thereto in such a way that the output of operational amplifier OP1 (FIG. 2), used as a comparator, switches at the zero crossings in the derivative waveform corresponding to major peaks in the ECG input signal. The output of comparator OP1 appears as waveform 104 in FIG. 3A, and illustrates the switching action just described.

Further referring to FIG. 2, transistor Q1 has its emitter connected to one of the offset adjustment terminals of operational amplifier OP1 so as to add hysteresis to the switching threshold of the amplifier OP1. This hysteresis, in combination with the characteristics of the low pass filter 19 of FIG. 1, has the effect of reducing the sensitivity of the heart rate circuit 21 to smaller peaks in the ECG input signal. As will be now described, the remainder of heart rate circuit 21 of FIG. 2 acts as a precision timer which is responsive to the ECG peaks, as detected by and indicated by switching of the operational amplifier OP1.

Specifically, a programmable uni-junction transistor Q2 is connected in series with resistor R5, the latter series combination being connected between the output of amplifier OP1 and the collector of transistor Q1. In addition, the gate lead of transistor Q2 is connected, via resistor R4 to the output of amplifier OP1. In short, programmable uni-junction transistor Q2 is connected in such a way as to provide a narrow pulse to the base of a further transistor Q3 having its base connected via resistors R7 and R8 to the uni-junction transistor Q2, as shown. The narrow pulse thus provided to the base of transistor Q3 corresponds to the rising edge of the output of amplifier OP1 (waveform 104 of FIG. 3A), and this narrow pulse is indicated by waveform 106 of FIG. 3A. The operation of programmable uni-junction transistor Q2, which thus provides the pulse output shown in waveform 106, will be evident to those of skill in the art with respect to the utilization of such devices.

The narrow pulse shown in waveform 106 of FIG. 3A is also shown in FIG. 3B. This narrow pulse is applied to the base of transistor Q3, and turns on transistor Q3 at a frequency determined by the frequency of occurrence of the rising edges of the output of amplifier OP1, that is, in accordance with a frequency related to heart rate. Thus, if the heart rate is sufficiently high, capacitor C2 will experience a voltage build-up as shown in waveform 108 of FIG. 3B. That is to say, capacitor C2 will experience a build-up of voltage under the influence of power supply $V_s$ (provided via resistors R9 and R10), and will then discharge through transistor Q3 when that transistor is turned on by receipt of a narrow pulse (waveform 106 of FIG. 3B) at the base of transistor Q3. Accordingly, since the voltage of C2, for high heart rate, will not reach the threshold voltage of programmable uni-junction transistor Q4, transistor Q4 will not conduct, and the gate voltage of transistor Q4 (that is, the voltage at the junction between resistors R11 and R12, diode D2 and transistor Q4) will remain high (see waveform 110 of FIG. 3B). Thus, the output INHIBIT of rate circuit 21 will remain high, and will not inhibit the PDF circuit 20 of FIG. 1.

Conversely, if the heart rate is low, conduction of transistor Q3 will be relatively less frequent, and capacitor C2 will charge to the point where transistor Q4 will "fire", thus discharging capacitor C2 therethrough. This charging and discharging of capacitor C2, under these conditions, is indicated by waveform 112 of FIG. 3A. When transistor Q4 "fires" in this manner, its gate lead is pulled low, and remains low until receipt of the next narrow pulse applied to the base of transistor Q3. Specifically, the next narrow pulse received at the base of transistor Q3 provides (as indicated in waveform 112 of FIG. 3A) a slight negative voltage on capacitor C2, and this slight negative voltage turns off transistor Q4, returning it to its non-conductive state. Accordingly, the voltage at the point between resistors R11 and R12, diode D2 and transistor Q4 returns to a positive polarity, as indicated by waveform 114 of FIG. 3A.

Thus, firing of transistor Q4 results in the occurrence of a negative-going pulse (waveform 114 of FIG. 3A) at the aforementioned junction between resistors R11 and R12, diode D2 and transistor Q4. Such negative-going pulses are utilized to inhibit operation of the PDF circuit 20 of FIG. 1 (via the control line INHIBIT). Specifically, these negative-going pulses are utilized to remove charge from the integrating capacitor in the PDF circuit 20, as taught in U.S. Pat. No. 4,184,493 of Langer et al.

To summarize, the operation of PDF circuit 20 (FIG. 1) is inhibited by rate circuit 21 at low heart rate, but no such inhibiting function takes place at high heart rate. Thus, at high heart rate, the PDF circuit 20 proceeds with its normal detection operation, and enables defibrillation pulse generator 26 in accordance therewith.

Further referring to FIG. 2, it is to be noted that diode D2 is provided for the purpose of temperature and voltage stabilization of the time interval of transistor Q4.

Referring back to FIG. 1, as mentioned earlier, interface 16 is a conventional interface. More specifically, interface 16 protects the ECG amplifier 18 from the defibrillation pulses issued by generator 26, while at the same time permitting the monitoring of heart activity by ECG amplifier 18. Interface 16 is, for example, disclosed in more detail in copending application U.S. Ser. No. 215,520 of Langer, entitled "Method and Apparatus for Combining Pacing and Cardioverting Functions in a Single Implanted Device." Moreover, the PDF circuit 20 is a conventional circuit for performing the probability density function, and is, for example, disclosed in more detail in the aforementioned U.S. Pat. Nos. 4,184,493 and 4,202,340 of Langer et al.

Figure 4:
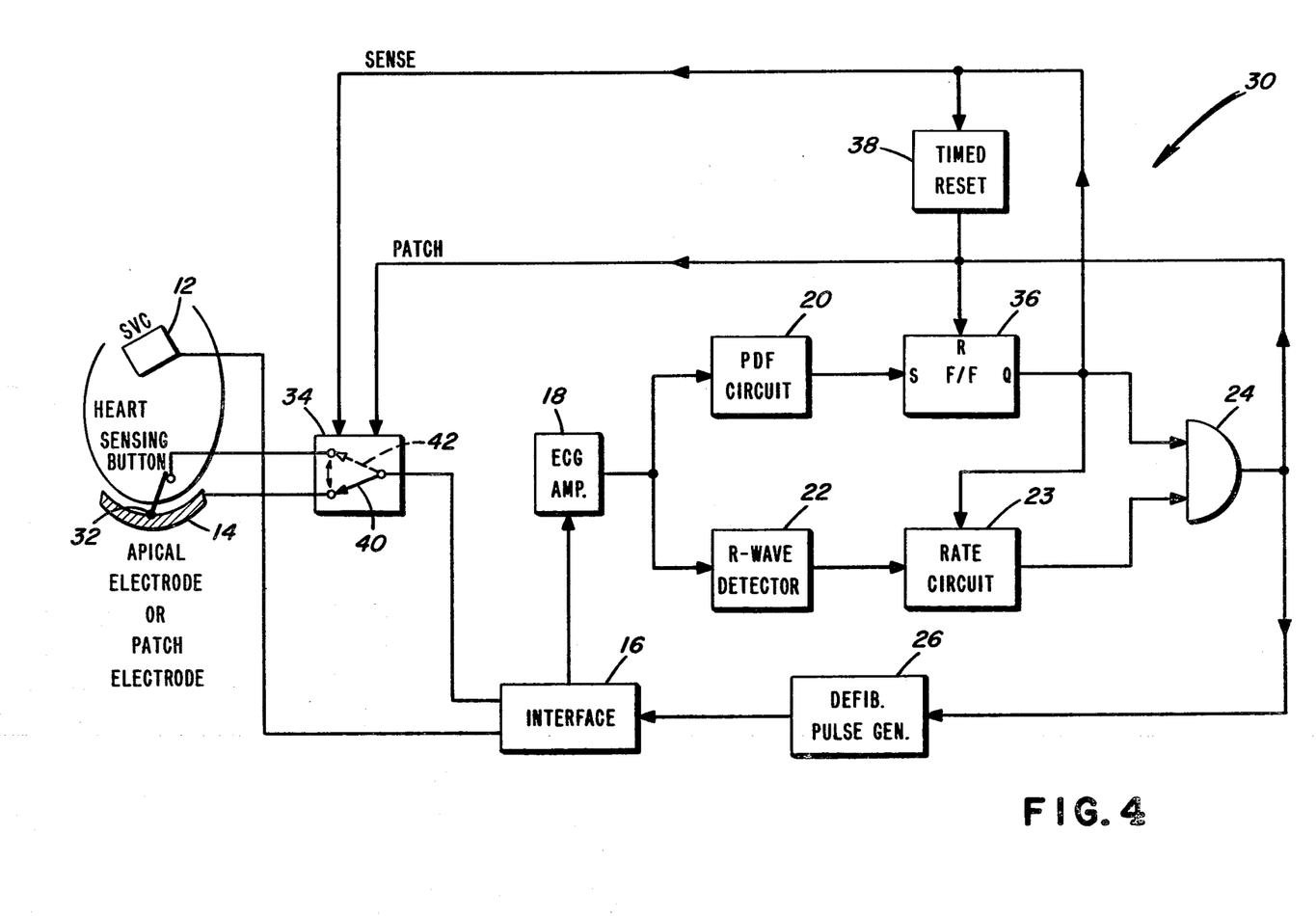
FIG. 4 is a block diagram of a second embodiment of the system of the present invention.

FIG. 4 is a block diagram of a second embodiment of the system of the present invention. Elements common to both FIGS. 1 and 4 have been identified by identical reference numerals.

Referring to FIG. 4, the system 30 is shown connected to base and apical electrodes 12 and 14, and to a sensing button 32 (associated with apical electrode 14). More specifically, the electrodes 12 and 14 and sensing button 32 are connected, via a switch 34 and interface 16, both to the ECG amplifier 18 and the defibrillation pulse generator 26. ECG amplifier 18 is connected, as was the case in FIG. 1, to the PDF circuit 20, but is also connected to R-wave detector 22 which is of conventional design and provides a pulse with each R-wave. R-wave detector 22 is subsequently connected to rate circuit 23, which is shown in detail in FIG. 5 (to be discussed below). The output of PDF circuit 20 is connected, via flip-flop 36, to one input of the AND gate 24, the other input of which is connected to the output of rate circuit 23. The output of flip-flop 36 is connected to rate circuit 23, the input of a timed reset circuit 38 (the output of which is connected to the "reset" input of flip-flop 36), and to switch 34. Moreover, the output of AND gate 24 is connected not only to defibrillation pulse generator 26, but also to the "reset" input of flip-flop 36 and to switch 34.

In operation, switch 34 is initially in the position indicated by reference numeral 40. Therefore, in this mode (subsequently referred to as the "patch" mode), the base and apical electrodes are utilized by ECG amplifier 18 which monitors heart activity via interface 16, switch 34, and aforementioned electrodes 12 and 14. The resulting ECG signal output from amplifier 18 is provided to PDF circuit 20 (rate circuit 23 is initially in the "off" state). Detection of abnormal cardiac rhythm by PDF circuit 20 results in generation of an output, which is applied to the "set" input of flip-flop 36. When flip-flop 36 is set, existence of abnormal cardiac rhythm is "memorized", and a Q output is generated.

The Q output of flip-flop 36 is applied as an "enabling input" to AND gate 24. It is also applied as a START command to both rate circuit 23 and timed reset circuit 38. Moreover, the Q output of flip-flop 36 is provided as signal SENSE to the switch 34, resulting in actuation of switch 34 to the position indicated by reference numeral 42. This establishes the "sense" mode of operation, during which heart rate is monitored by rate circuit 23. More specifically, actuation of switch 34 to the position indicated by reference numeral 42 connects the interface 16 to the sensing button 32, so that heart rate can be monitored by rate circuit 23 via R-wave detector 22, switch 34, interface 16, and ECG amplifier 18. Since the ECG amplifier 18 is connected to a very small surface area electrode, sharp depolarizations will still be delivered to R-wave detector 22, resulting in a proper signal indication of heart rate. It will be recalled that rate circuit 23 was started by the Q output of flip-flop 36, the latter being issued as a result of detection of abnormal cardiac rhythm (satisfaction of the probability density function criteria) by PDF circuit 20.

If and when rate circuit 23 detects a heart rate which exceeds a predetermined threshold, it issues an output to AND gate 24 which, as enabled by the Q output of flip-flop 36, provides this output as an enabling input to defibrillation pulse generator 26. Moreover, AND gate 24 provides this output to the "reset" input of flip-flop 36 (thus, resetting flip-flop 36), and as an input signal PATCH to switch 34, actuating switch 34 to the position indicated by reference numeral 40, thus reestablishing the "patch" mode of operation of the system 30. Finally, defibrillation pulse generator 26, as enabled by AND gate 24, issues a defibrillation pulse, via interface 16 and switch 34 (in position 40), to the base and apical electrodes 12 and 14, respectively, so as to defibrillate the heart of the patient.

As previously mentioned, the Q output of flip-flop 36 starts the timed reset circuit 38 upon detection of abnormal cardiac rhythm by the PDF circuit 20. If, after a predetermined period of time, rate circuit 23 has not detected a heart rate above the predetermined threshold, timed reset circuit 38 automatically issues a "reset"

input to flip-flop 36, and provides a further input PATCH to the switch 34, so as to actuate switch 34 to the position indicated by reference numeral 40, thus reestablishing the "patch" mode of operation. Accordingly, the system 30 is provided with the beneficial feature whereby if, within a predetermined time after detection of abnormal cardiac rhythm by PDF circuit 20, heart rate is not detected as exceeding the predetermined threshold, the system 30 is returned to the "patch" mode of operation so as to permit further monitoring of the ECG signal by the PDF circuit 20. That is to say, the timed reset circuit 38 removes the enabling input from AND gate 24, turns off the rate circuit 23, and returns the switch 34 to the "patch" position (indicated by reference numeral 40). Then the PDF circuit 20 monitors the base and apical electrodes 12 and 14, respectively, via switch 34, interface 16 and ECG amplifier 18, to once again detect existence of any abnormal cardiac rhythm.

Figure 5:
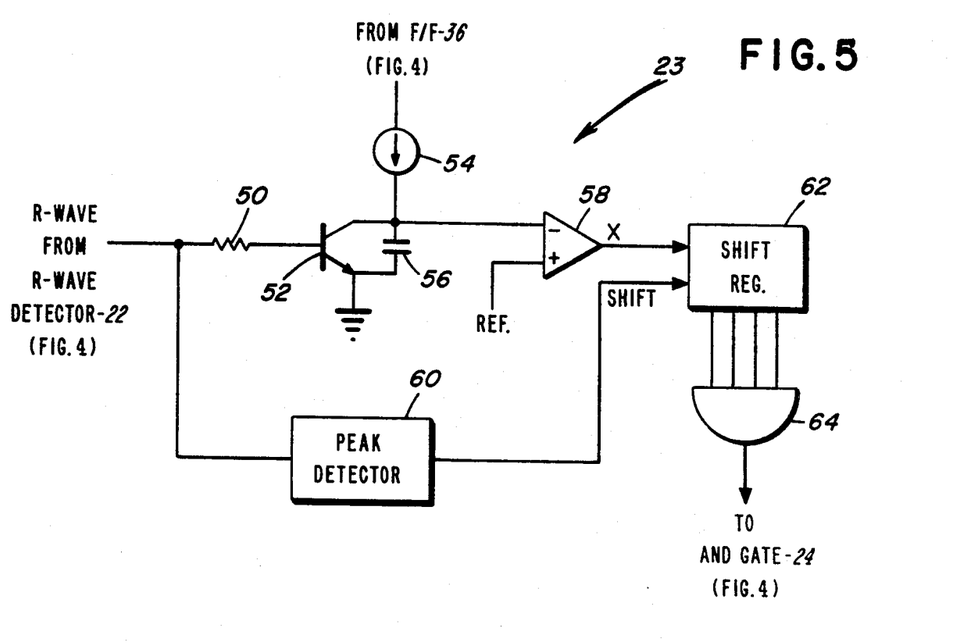
FIG. 5 is a detailed diagram of the heart rate circuit employed for detecting heart rate in the embodiment of FIG. 2.
Figure 6:
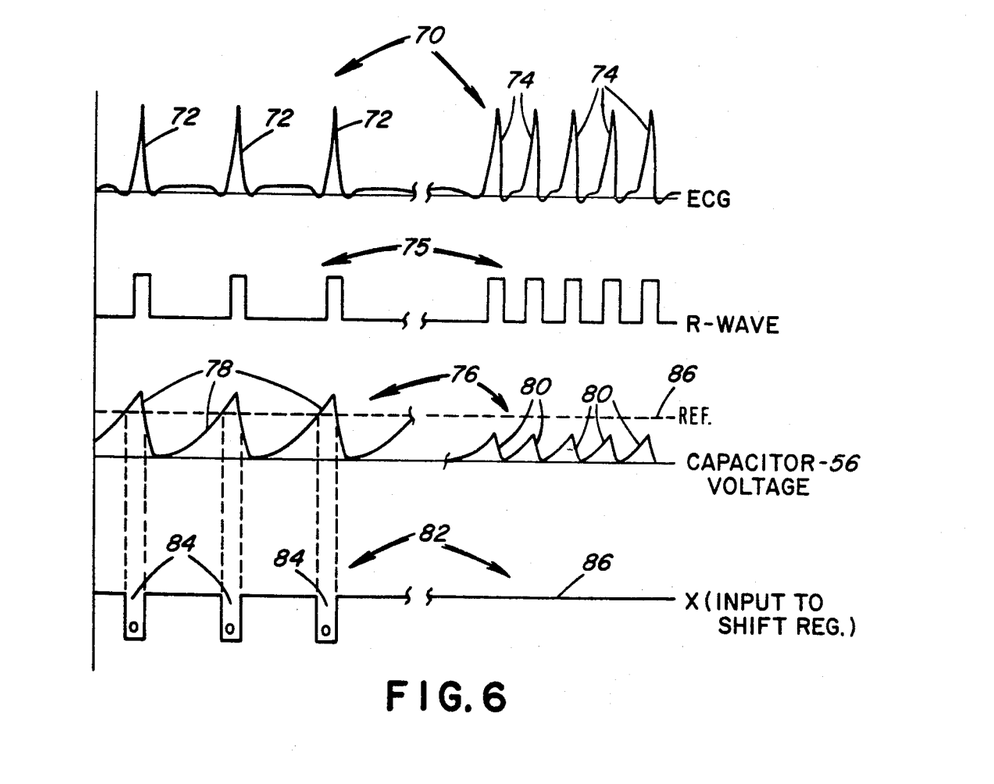
FIG. 6 is a series of waveform diagrams utilized in describing the operation of the heart rate circuit of FIG. 5.

FIG. 5 is a detailed diagram of the heart rate circuit 23 of FIGS. 4, while FIG. 6 is a series of waveform diagrams describing the operation of the heart rate circuit 23 of FIG. 4. As seen in FIG. 5, rate circuit 23 comprises input resistor 50, NPN transistor 52, current source 54, capacitor 56, differential amplifier or comparison circuit 58, peak detector 60, shift register 62 and AND gate 64.

In operation, ECG signals (generally indicated by reference numeral 70 of FIG. 6 and shown, for each of the two discrete segments, as having regular R-waves and a generally stable rate) are provided to R-wave detector 22 (FIG. 4), the latter generating a pulse train (generally indicated by reference numeral 75 of FIG. 6) corresponding thereto. Specifically, this pulse train output of the R-wave detector 22 is provided, via input resistor 50 (FIG. 5), to the base of NPN transistor 52. Transistor 52 is turned on as a result of receipt of each individual pulse in pulse train 75, and is thus turned on in correspondence to detection of individual R-waves 72, 74. During those periods of time between individual R-waves 72 (or 74) in FIG. 6, transistor 52 is non-conductive, and current source 54 builds up a voltage on capacitor 56. This build-up of voltage on capacitor 56 is generally indicated by waveform 76 of FIG. 6.

However, upon occurrence of an R-wave 72 or 74, NPN transistor 52 (FIG. 5) becomes conductive, and capacitor 56 discharges therethrough (see individual waveforms 78 and 80 of FIG. 6). Thus, it can be seen that, for a normal heart rate (as indicated by waveforms 72 of FIG. 6), capacitor 56 discharges at a relatively low frequency of discharge; thus, current source 54 is able to build the voltage across capacitor 56 to a relatively high level, exceeding a predetermined reference REF (indicated by reference numeral 86 in FIG. 6). Conversely, occurrence of R-waves at an abnormally high rate (as indicated by waveforms 74 of FIG. 6) results in discharge of capacitor 56 at a more frequent rate (as indicated by waveforms 80 of FIG. 6), and the reference REF is not exceeded.

Further referring to FIG. 5, it is seen that differential amplifier 58 is provided, at its negative input, with a voltage corresponding to the voltage built up on capacitor 56, and, at its positive input, with a voltage REF corresponding to the predetermined reference level 86 of FIG. 6. Thus, referring to FIGS. 5 and 6, whenever the voltage on capacitor 56 exceeds the predetermined reference 86 (as in waveforms 78), differential amplifier 58 issues an output X equal to 0, as indicated by inverted square waves 84 of FIG. 6, to the shift register 62. Conversely, during those periods of time when the voltage across capacitor 56 does not exceed the reference 86 (as in waveforms 80 of FIG. 6), differential amplifier 58 issues an output X equal to 1 to the shift register 62.

Rate circuit 23 of FIG. 5 is further provided with a peak detector 60, which is a conventional circuit for detecting the existence of peaks in the R-waves 70 of FIG. 6. Upon detection of each peak, detector 60 issues an input SHIFT to shift register 62. As a result, the output X, at that time, of differential amplifier 58 is shifted into an end stage of shift register 62, the contents of register 62 being accordingly shifted by one place to the right.

Furthermore, the output of shift register 62 (corresponding to the contents of each bit or stage thereof) is provided to AND gate 64. Only detection of all 1's in shift register 62 will result in an output from AND gate 64. This output of AND gate 64 is provided to one input of AND gate 24 (FIG. 4), the other input of which receives the Q output of flip-flop 36, indicating satisfaction of the probability density function criteria, as determined by PDF circuit 20. As a result, with both the probability density function criteria having been satisfied and an excessive heart rate having been detected, AND gate 24 enables defibrillation pulse generator 26, so as to issue a defibrillation pulse to the heart of the patient. Conversely, so long as any of the bits of shift register 62 are 0 in value, AND gate 64 does not issue an output, indicating that a consistently high heart rate has not been detected by rate circuit 23. Thus, shift register 62 provides a means of remembering the rates of previous beats. (It should be evident that the greater the number of bits in the shift register, the higher is the number of R-waves which must exceed a given rate before a high rate is indicated.) Thus, defibrillation does not take place, even if the probability density function is satisfied.

While preferred forms and arrangements have been shown in illustrating the invention, it is to be clearly understood that various changes in detail and arrangement may be made without departing from the spirit and scope of this disclosure.

What is claimed is:

1. A method for delivering defibrillating energy to the heart of a patient experiencing abnormal cardiac rhythm, including ventricular fibrillation, which is characterized by an irregular ECG waveform, and high rate tachycardia and low rate tachycardia, both of which are characterized by regular R-waves occurring at generally stable rates, the deliverance of defibrillating energy taking place irrespective of the regularity of the ECG waveform representing such abnormal cardiac rhythm, said method comprising the steps of:

monitoring an ECG signal from the heart of the patient;

examining said ECG signal to detect said abnormal cardiac rhythm including ventricular fibrillation, high rate tachycardia, and low rate tachycardia;

examining said ECG signal to sense heart rate so as to distinguish between ventricular fibrillation and high rate tachycardia, on the one hand, and low rate tachycardia, on the other hand, said distinguishing being made without regard to the regularity or lack of regularity of the ECG waveform corresponding to said ECG signal;

issuing a defibrillating signal when both examining steps sense ventricular fibrillation or high rate tachycardia;

not issuing a defibrillating signal when both examining steps sense low rate tachycardia or normal sinus rhythm; and responding to said defibrillating signal by automatically delivering defibrillating energy to the heart of the patient.

2. The method of claim 1, wherein said monitoring step comprises sensing an electrocardiograph (ECG) of the heart to develop ECG data, and said first recited examining step comprises processing said ECG data in accordance with a probability density function.

3. The method of claim 1, comprising the additional step, prior to said monitoring step, of connecting a base electrode and an apical electrode to said heart, said base and apical electrodes being used during said monitoring step.

4. The method of claim 1, comprising the additional step, prior to said monitoring step, of connecting a base electrode, an apical electrode and a sensing button to said heart, said base and apical electrodes being used during said monitoring step, and said sensing button being used during said monitoring step.

5. The method of claim 1, wherein said two examining steps are performed simultaneously.

6. The method of claim 5, wherein said monitoring step comprises sensing an electrocardiograph (ECG) of the heart to develop ECG data, and said first recited examining step comprises processing said ECG data in accordance with a probability density function to produce a detection output when said abnormal cardiac rhythm is detected, said method comprising the additional step of inhibiting said detection output when said sensing step determines the presence of low rate tachycardia.

7. The method of claim 1, wherein said first recited examining step and said second recited examining step are performed in sequence, said second recited examining step being performed only when said abnormal cardiac rhythm is detected during said first examining step.

8. The method of claim 7, comprising the additional step, prior to said monitoring step, of connecting a base electrode, an apical electrode and a sensing button to said heart, said base and apical electrodes being used during said detecting step, and said sensing button being used during said sensing step.

9. The method of claim 1, wherein said second recited examining step comprises comparing the heart rate of the heart to a predetermined threshold, said step of automatically delivering defibrillating energy to the heart being executed when said heart rate exceeds said predetermined threshold.

10. The method of claim 9, wherein said second recited examining step further comprises automatically returning to said first recited examining step when said heart rate remains below said predetermined threshold for a predetermined time.

11. A system for delivering defibrillating energy to the heart of a patient experiencing abnormal cardiac rhythm including ventricular fibrillation which is characterized by an irregular ECG waveform, and high rate tachycardia and low rate tachycardia, both of which are characterized by regular R-waves occurring at generally stable rates, the deliverance of defibrillating energy taking place irrespective of the regularity of the ECG waveform representing such abnormal cardiac rhythm, said system comprising:

monitoring means for deriving an ECG signal from the heart of the patient;

detecting means, receiving said ECG signal from said monitoring means for detecting said abnormal cardiac rhythm, said abnormal cardiac rhythm including ventricular fibrillation, high rate tachycardia, and low rate tachycardia, said detecting means normally issuing a defibrillating signal upon detection of said abnormal cardiac rhythm;

automatic defibrillating means responsive to said defibrillating signal for automatically delivering defibrillating energy to the heart of the patient;

sensing means receiving said ECG signal from said monitoring means and simultaneously operative with said detecting means for sensing heart rate so as to distinguish between ventricular fibrillation and high rate tachycardia, on the one hand, and low rate tachycardia, on the other hand, said distinguishing being made without regard to the regularity or lack of regularity of the ECG waveform corresponding to said ECG signal; and means responsive to said sensing of said ventricular fibrillation and high rate tachycardia by said sensing means for permitting said defibrillating signal to activate said automatic defibrillating means and responsive to said sensing of lowa rate tachycardia by said sensing means for preventing deliverance of said defibrillating signal to said automatic defibrillating means.

12. The system of claim 11, wherein said monitoring means comprises a sensing circuit for sensing an electrocardiograph (ECG) of the heart to develop ECG data, and said detecting means comprises processing means for processing said ECG data in accordance with a probability density function.

13. The system of claim 11, further comprising a base electrode and an apical electrode connected to said heart, and means for connecting said base and apical electrodes to said detecting means and said sensing means.

14. The system of claim 11, wherein said monitoring means comprises a sensing circuit for sensing an electrocardiograph (ECG) of the heart to develop ECG data, and said sensing means comprising a low pass filter circuit connected to said sensing circuit for low pass filtering said ECG data to provide a low pass filter output, said sensing means further comprising a rate circuit connected to said low pass filter circuit for receiving said low pass filter output and responsive thereto for sensing the heart rate.

15. The system of claim 11, wherein said detecting means and said sensing means operate simultaneously, said detecting means including a processing circuit for processing said ECG signal in accordance with a probability density function to develop a detection output, said sensing means comprising a rate circuit responsive to detection of low rate tachycardia for inhibiting said detection output of said processing circuit, whereby to inhibit automatic defibrillation of the heart of the patient upon detection of said low rate tachycardia.

16. The system of claim 11, wherein said monitoring means comprises a base electrode, an apical electrode and a sensing button connected to said heart, and said system further comprises connecting means for connecting said base and apical electrodes to said detecting means, and for connecting said sensing button to said sensing means.

17. The system of claim 16, wherein said connecting means comprises a switch circuit having a first state and a second state, said switch circuit being initially in said first state during operation of said detecting means for detecting said abnormal cardiac rhythm, said switch circuit being responsive to detection of said abnormal cardiac rhythm by said detecting means so as to be actuated to said second state, said switch circuit being responsive to determination of one of said ventricular fibrillation and said high rate tachycardia so as to be actuated to said first state for automatic defibrillation of the heart of the patient by said automatic defibrillating means.

18. The system of claim 17, wherein said detecting means comprises a probability density function circuit for determining when said abnormal cardiac rhythm exists, and a bistable circuit connected to said probability density function circuit and responsive to determination of the existence of said abnormal cardiac rhythm by said probability density function circuit for being actuated to a first state so as to emit a first output indicating existence of said abnormal cardiac rhythm.

19. The system of claim 18, further comprising means for providing said first output of said bistable circuit to said switch circuit, said switch circuit being responsive thereto for being actuated to said second state.

20. The system of claim 19, further comprising timed reset circuit means for automatically resetting said bistable circuit, and means for providing said first output of said bistable circuit to said timed reset circuit means for actuating said timed reset circuit means to start counting to a predetermined final count, said timed reset circuit means resetting said bistable circuit upon reaching of said predetermined final count.

21. The system of claim 18, wherein said sensing means comprises a heart rate circuit responsive to said first output of said bistable circuit for starting a heart rate monitoring operation.

22. The system of claim 21, wherein said heart rate circuit issues a first output when said monitored heart rate of the patient exceeds a predetermined threshold.

23. The system of claim 22, further comprising AND gate means responsive to said first output of said bistable circuit and said first output of said heart rate circuit for actuating said automatic defibrillating means to defibrillate the heart of the patient.

24. The system of claim 23, wherein said AND gate means is responsive to said first output of said bistable circuit and said first output of said heart rate circuit for actuating said switch circuit to said first state.

25. The system of claim 23, wherein said AND gate means is responsive to said first output of said bistable circuit and said first output of said heart rate circuit for automatically resetting said bistable circuit.

26. The system of claim 18, further comprising timed reset circuit means responsive to issuance of said first output by said bistable circuit for starting a counting operation so as to count to a final count value, said timed; reset circuit means being responsive to reaching of said final count value for resetting said bistable circuit.

27. The system of claim 17, wherein said switch circuit, in said first state, connects said base and apical electrodes to said detecting means, and, in said second state, connects said sensing button to said sensing means, 28. The system of claim 17, further comprising interface means for interfacing said switch circuit to said detecting means and said sensing means, said switch circuit, in said first state, connecting said base and apical electrodes to said interface means, and, in said second state, connecting said sensing button to said interface means.

29. The system of claim 28, further comprising an ECG amplifier for connecting said interface means, on the one hand, to said detecting means and said sensing means, on the other hand.

30. The system of claim 17, further comprising an ECG amplifier for connecting said switch circuit, on the one hand, to said detecting means and said sensing means, on the other hand.

31. The system of claim 11, wherein said monitoring means comprises an ECG input circuit for sensing an ECG of the heart to develop ECG data, and said detecting means comprises a processing circuit for processing said ECG data in accordance with a probability density function, and for issuing a first output when said probability density function is satisfied, said detecting means further comprising a bistable circuit responsive to said first output of said processing circuit for issuing a further output signal indicating detection of said abnormal cardiac rhythm.

32. The system of claim 31, wherein said monitoring means comprises a base electrode, an apical electrode, and a sensing button connected to said heart, and said system further comprises connecting means for initially connecting said base and apical electrodes to said ECG input circuit, said connecting means being responsive to said further output signal from said bistable circuit for connecting said sensing button to said sensing means.

33. The system of claim 31, wherein said sensing means comprises a heart rate circuit for monitoring the heart rate of the patient, said heart rate circuit being responsive to said further output signal from said bistable circuit for beginning its heart rate monitoring operation.

34. The system of claim 33, wherein said heart rate circuit issues an output signal when said heart rate exceeds a predetermined threshold, said system further comprising AND gate means responsive to said further output signal from said bistable circuit and said output signal of said heart rate circuit for issuing an output signal actuating said automatic defibrillating means to defibrillate the heart of the patient.

35. The system of claim 34, further comprising means for providing said output-signal of said AND gate means to said bistable circuit, said bistable circuit being responsive thereto for resetting itself so as to stop issuing said further output signal.

36. The system of claim 34, further comprising a base electrode, an apical electrode, and a sensing button, and connecting means for initially connecting said base and apical electrodes to said ECG input circuit, said connecting means being responsive to said further output signal of said bistable circuit for connecting said sensing button to said heart rate circuit.

37. The system of claim 36, further comprising means for providing said output signal of said AND gate means to said connecting means, said connecting means being responsive to said output signal of said AND gate means for connecting said base and apical cup electrodes to said automatic defibrillating means.

* * * * *